(12) United States Patent
Ingram et al.

(10) Patent No.: US 6,905,478 B2
(45) Date of Patent: Jun. 14, 2005

(54) NON-REUSABLE SYRINGE

(75) Inventors: Bruce Wallace Ingram, East Hawthorn (AU); Jodie Leigh Gartner, Mount Dandenong (AU)

(73) Assignee: Glenord Pty. Ltd., Caulfield South (AU)

( * ) Notice: Subject to any disclaimer, the term of this patent is extended or adjusted under 35 U.S.C. 154(b) by 0 days.

(21) Appl. No.: 10/471,813

(22) PCT Filed: Mar. 14, 2002

(86) PCT No.: PCT/AU02/00297
§ 371 (c)(1),
(2), (4) Date: Mar. 15, 2004

(87) PCT Pub. No.: WO02/072182
PCT Pub. Date: Sep. 19, 2002

(65) Prior Publication Data
US 2004/0147875 A1 Jul. 29, 2004

(30) Foreign Application Priority Data
Mar. 14, 2001 (AU) .............................. PR3730

(51) Int. Cl.⁷ .................................................. A61M 5/00
(52) U.S. Cl. ...................................... 604/110; 604/187
(58) Field of Search ................................ 604/110, 192, 604/198, 187, 263, 218, 220, 221, 222, 135, 136

(56) References Cited

U.S. PATENT DOCUMENTS

| 4,413,237 A | 11/1983 | Baba |
| 4,850,968 A | 7/1989 | Romano |
| 4,894,055 A | 1/1990 | Sudnak |
| 4,994,034 A | 2/1991 | Botich et al. |
| 5,053,010 A | 10/1991 | McGary et al. |
| 5,114,410 A | 5/1992 | Caralt Batlle |
| 5,122,118 A | 6/1992 | Haber et al. |
| 5,163,918 A | 11/1992 | Righi et al. |
| 5,180,369 A | 1/1993 | Dysarz |
| 5,211,628 A | 5/1993 | Marshall |
| 5,267,976 A | 12/1993 | Guerineau et al. |
| 5,342,310 A | 8/1994 | Ueyama et al. |
| 5,385,551 A | 1/1995 | Shaw |
| 5,423,758 A | 6/1995 | Shaw |
| 5,433,712 A | 7/1995 | Stiles et al. |
| 5,578,011 A | 11/1996 | Shaw |
| 5,632,733 A | 5/1997 | Shaw |
| 5,853,390 A | 12/1998 | Freschi |
| 5,855,839 A | 1/1999 | Brunel |

(Continued)

FOREIGN PATENT DOCUMENTS

| EP | 0 966 983 | 12/1999 |
| FR | 2 650 187 | 2/1991 |
| WO | WO 00/76565 | 12/2000 |

*Primary Examiner*—Manuel Mendez
(74) *Attorney, Agent, or Firm*—Andrus, Sceales, Starke & Sawall, LLP

(57) ABSTRACT

A single use syringe (10) has an outer barrel (11) and an inner barrel (12) slidable within the outer barrel. The two barrels are initially latched together to prevent relative movement therebetween whereby the syringe is in a useable condition. A needle (16) is in fluid communication with the inner barrel and projects initially from a first end of the outer barrel. A plunger (21) in the inner barrel is connected to a plunger actuating rod (22) which extends out the other end of the outer barrel. On first depression of the plunger actuating rod a limit catch (23) prevents full depression thereof but allows sufficient depression to draw fluid into the inner barrel. On the second depression the fluid is ejected and the plunger actuating rod and plunger are allowed full travel whereby latching between the two barrels is disengaged. It is not possible to re-latch the barrels together in the useable condition and therefore further use of the syringe is not possible. The needle retracts into the outer barrel after said first use and is locked therein.

11 Claims, 10 Drawing Sheets

U.S. PATENT DOCUMENTS

| | | |
|---|---|---|
| 5,911,705 A | 6/1999 | Howell |
| 5,989,220 A | 11/1999 | Shaw et al. |
| 6,186,980 B1 | 2/2001 | Brunel |
| 6,368,303 B1 | 4/2002 | Caizza |
| 6,409,701 B1 | 6/2002 | Cohn et al. |
| 6,432,087 B1 | 8/2002 | Hoeck et al. |
| 6,494,863 B1 | 12/2002 | Shaw et al. |
| 6,554,796 B2 | 4/2003 | Lo |
| 6,558,357 B1 | 5/2003 | Hoeck |
| 6,569,115 B1 | 5/2003 | Barker et al. |
| 6,572,584 B1 | 6/2003 | Shaw et al. |
| 6,585,690 B1 | 7/2003 | Hoeck et al. |
| 6,599,268 B1 | 7/2003 | Townsend et al. |
| 6,648,856 B1 | 11/2003 | Argento |
| 2001/0053886 A1 | 12/2001 | Caizza |

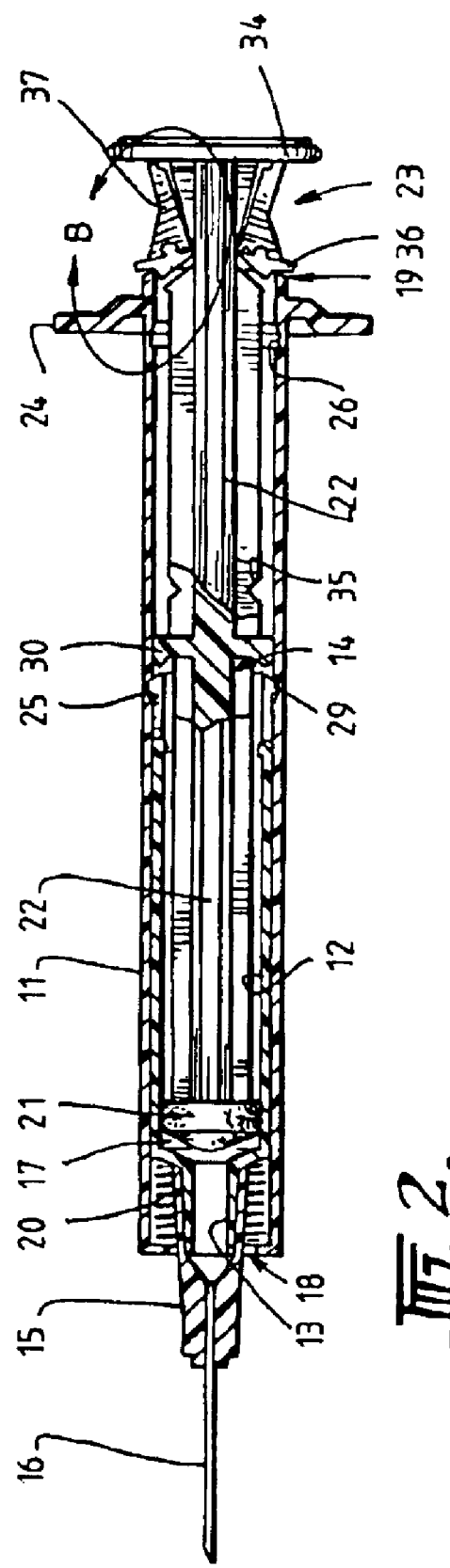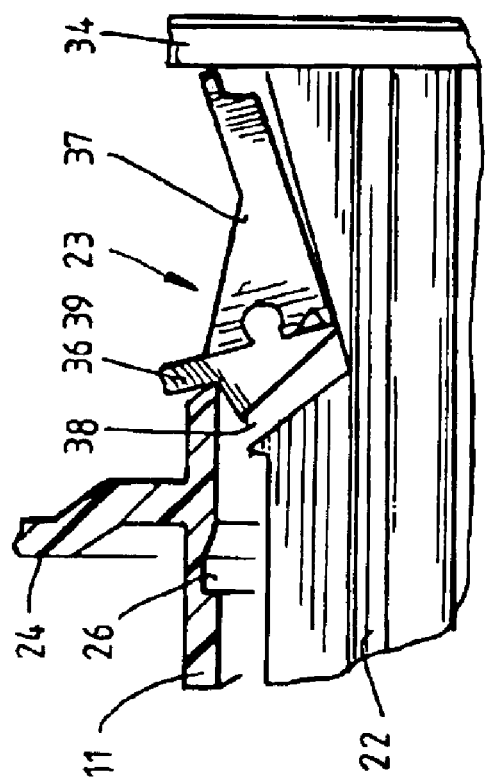
FIG. 2.
FIG. 2a.

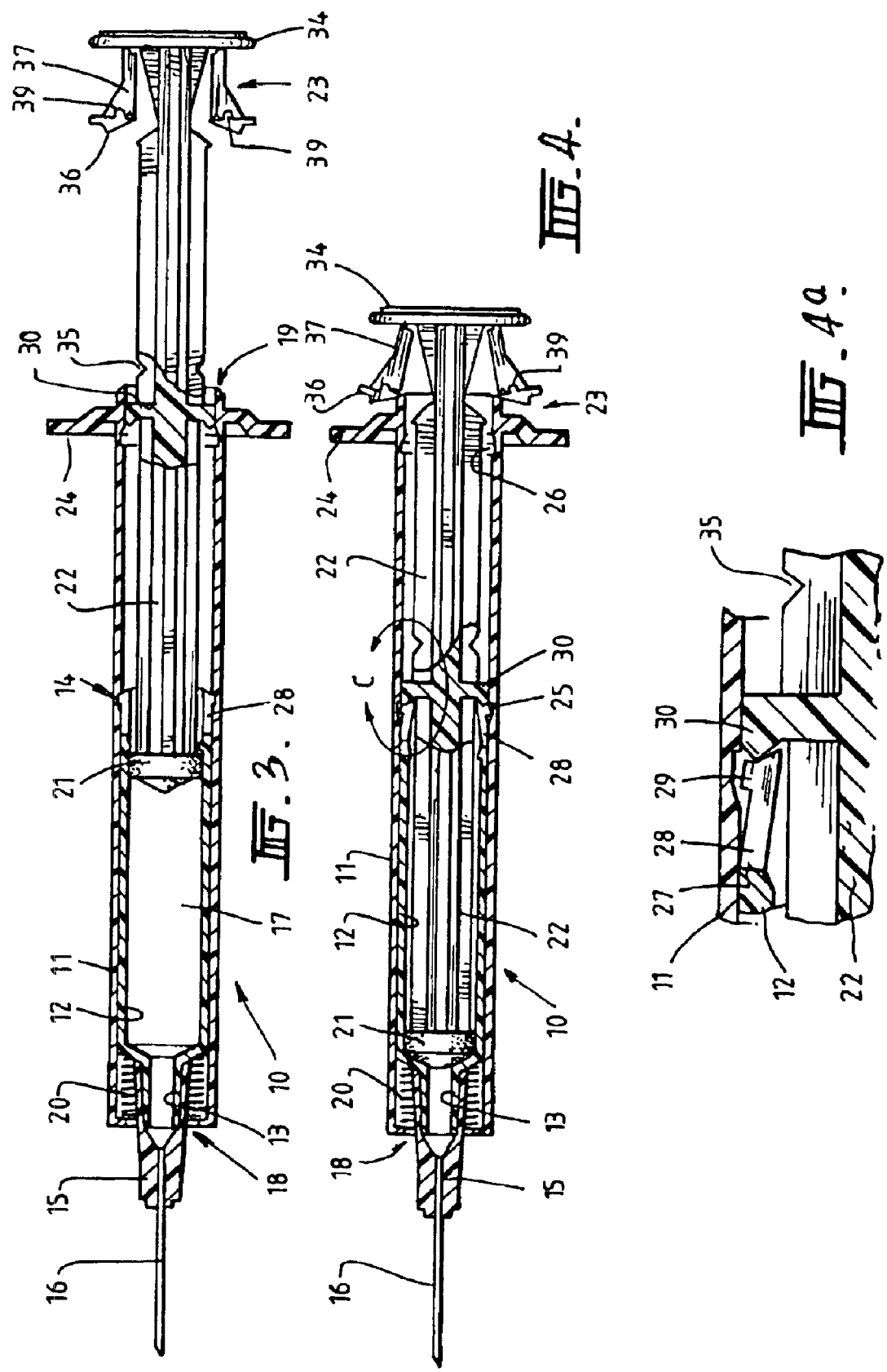

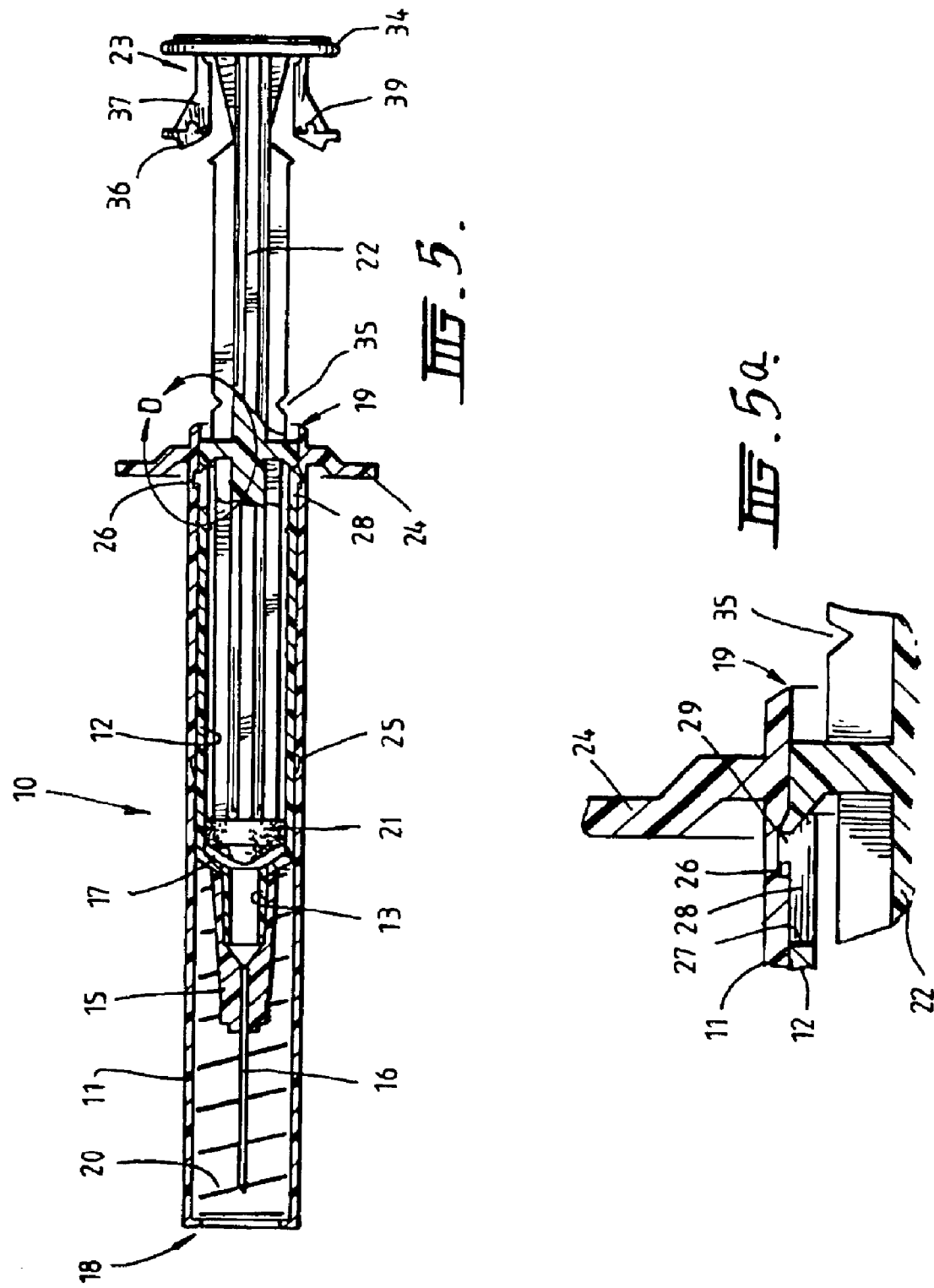

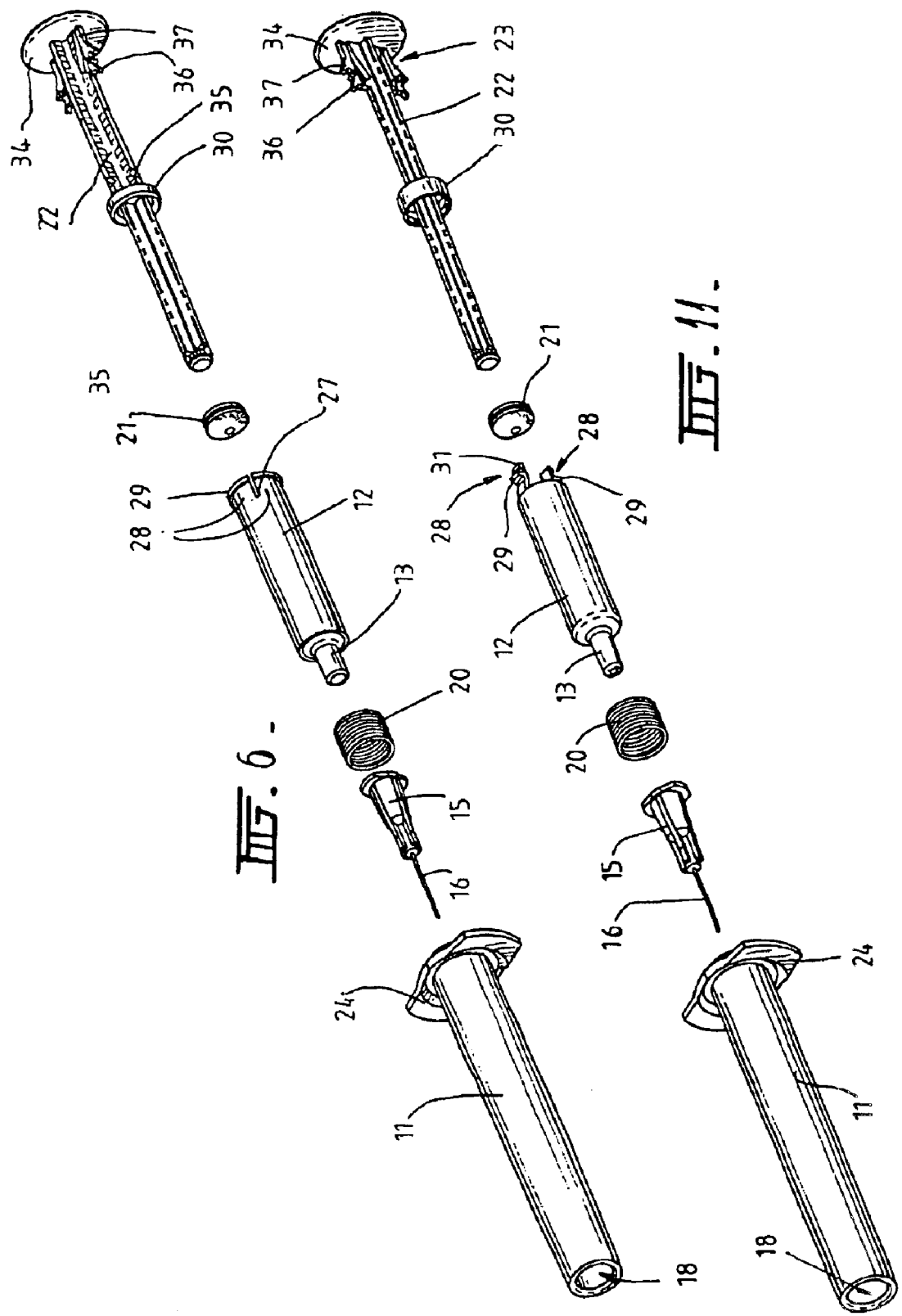

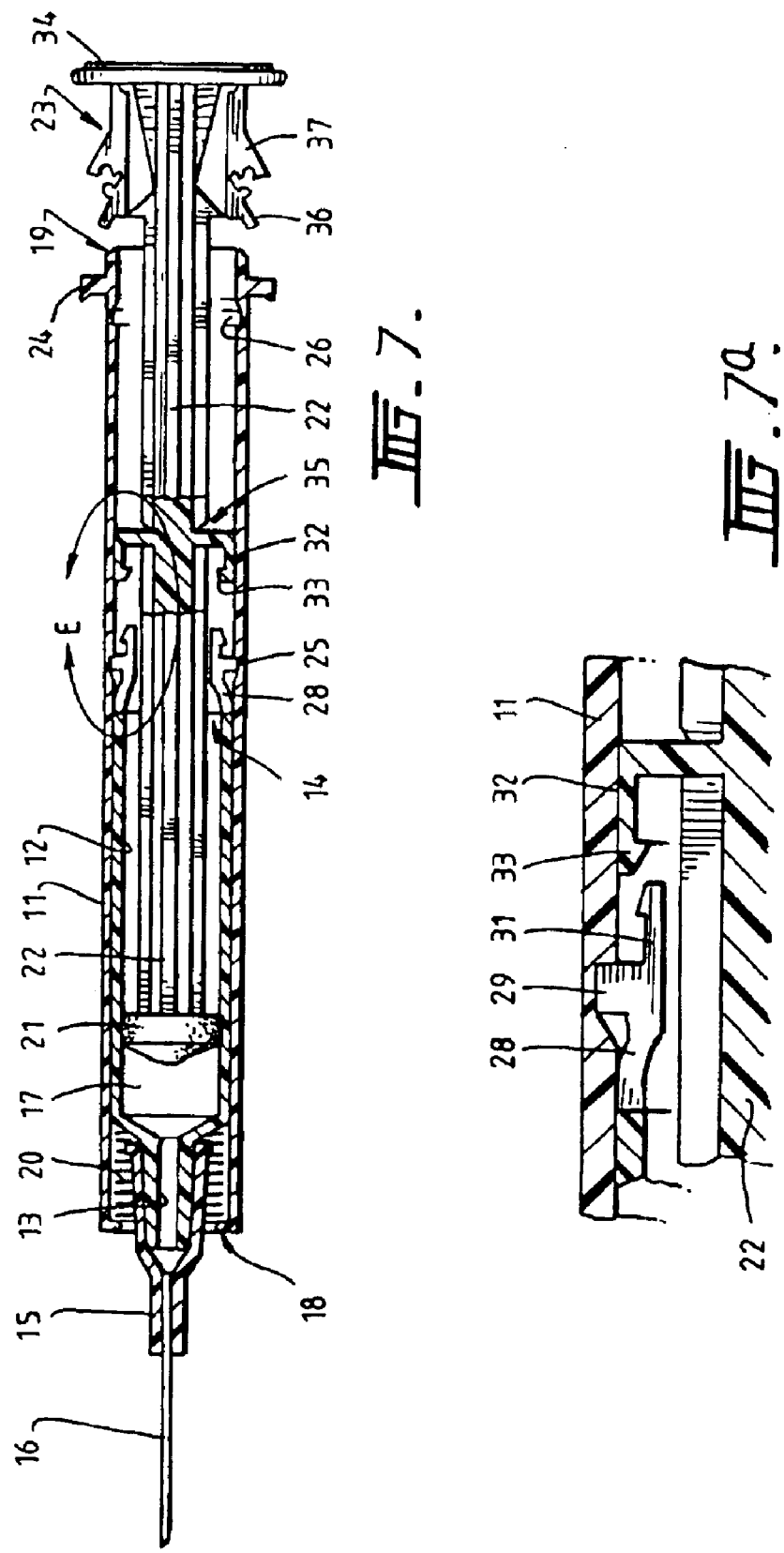

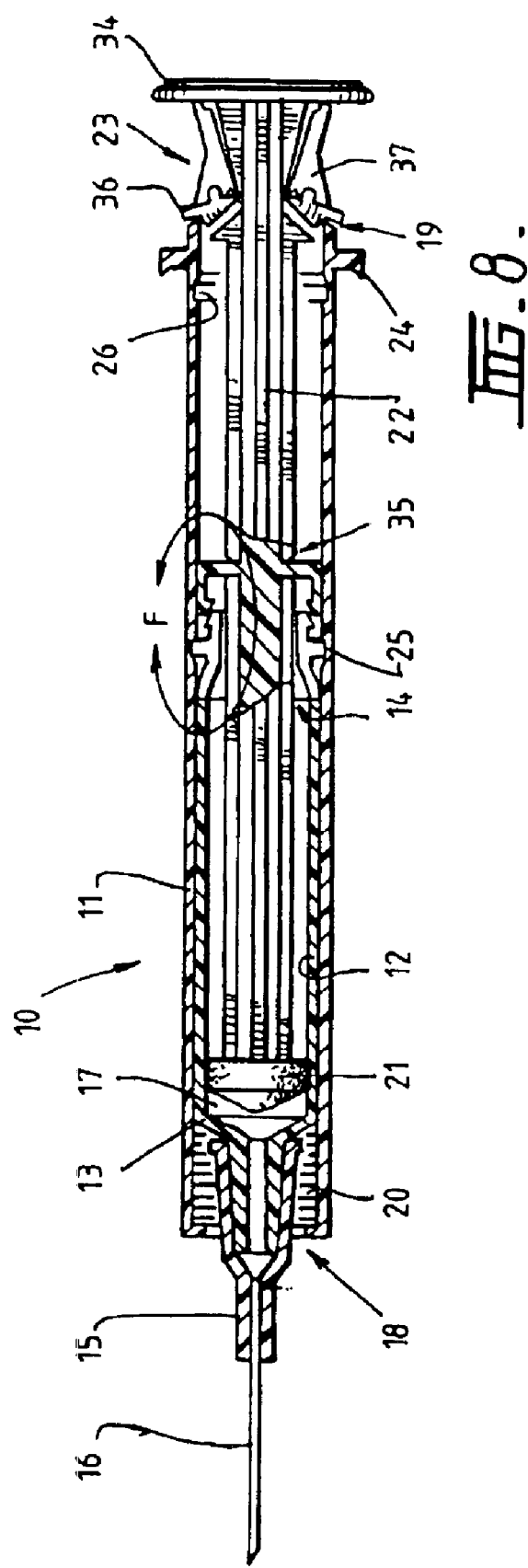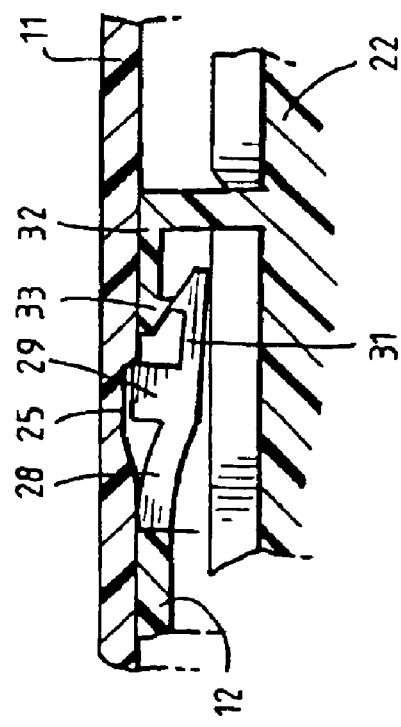

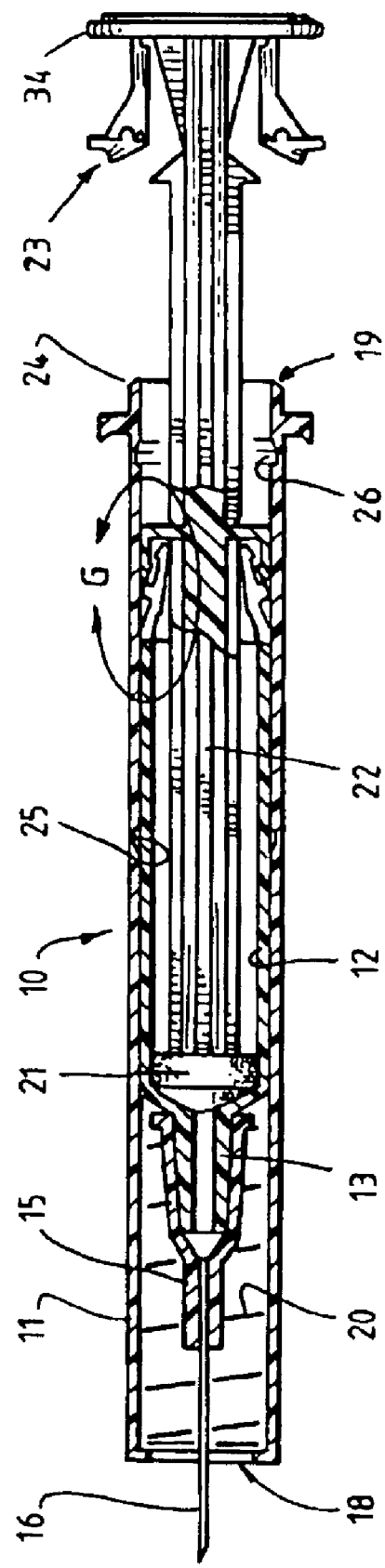
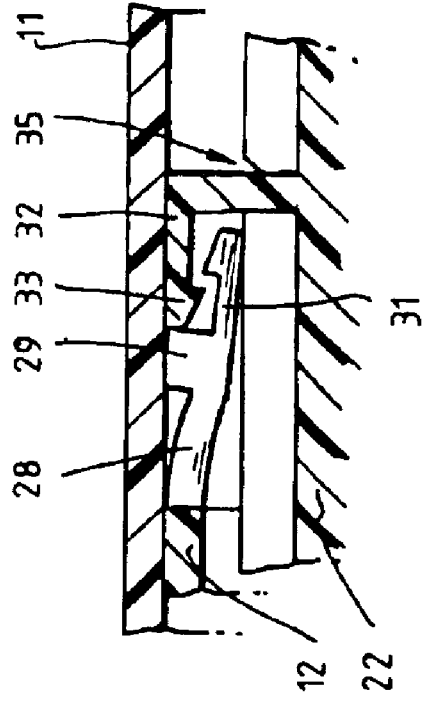
FIG. 9.
FIG. 9a.

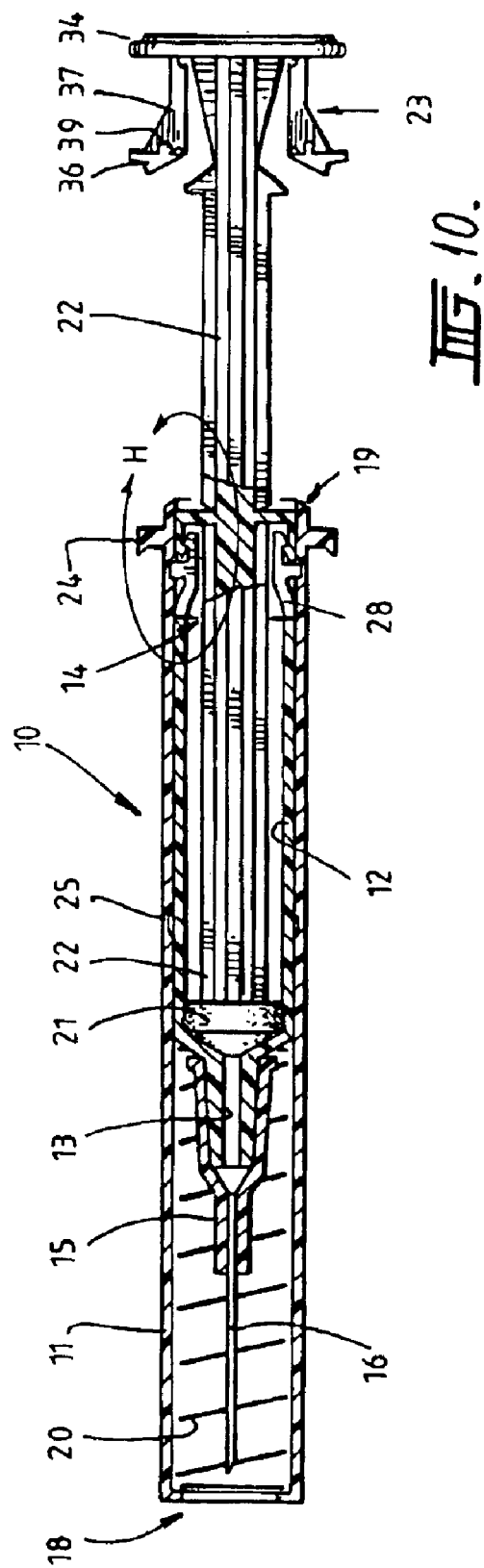
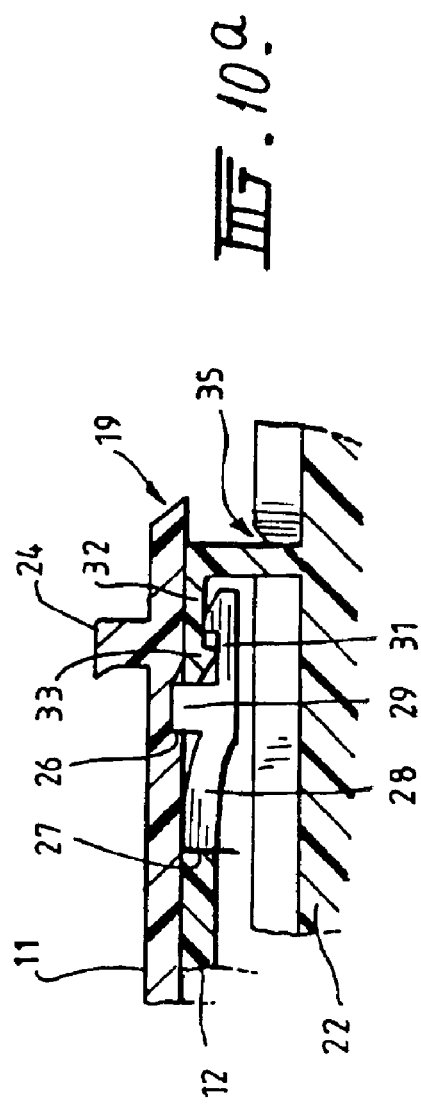
FIG. 10.
FIG. 10a.

NON-REUSABLE SYRINGE

CROSS REFERENCE TO RELATED APPLICATION

The present application is the U.S. national stage application of International Application PCT/AU02/00297, filed Mar. 14, 2002, which international application was published on Sep. 19, 2002 as International Publication WO 02/072182. The International Application claims priority of Australian Patent Application PR 3730, filed Mar. 14, 2001.

FIELD OF THE INVENTION

The invention relates to syringes and in particular to single use or non-reusable syringes with automatic retracting needle.

BACKGROUND OF THE INVENTION

The hazards to the general public and medical staff due to needle sticks from used syringes, as well as the problems associated with re-use of syringes by intravenous drug users is well documented. Many prior attempts have been made to provide a syringe which is capable of only a single use and which, after such use is self destructing or provides protection against needle sticks. One such syringe is disclosed in U.S. Pat. No. 5,267,976 for example. Generally speaking the prior art devices suffer one or more disadvantages in that they are too costly to manufacture, are unreliable, are easily tampered with or rely on the user taking some positive action after first use, to ensure that the syringe is disabled from further use. In prior art devices which have an automatically retracting needle such as that disclosed in aforementioned U.S. Pat. No. 5,267,976 there is also the possibility of premature retraction of the needle such as when the plunger is moved from its packaged position in preparation for drawing a drug into the syringe.

SUMMARY OF THE INVENTION

Accordingly it is an object of this invention to provide a single use syringe with self-retracting needle which overcomes one or more of the aforementioned and other disadvantages of known devices.

The invention provides a syringe including an outer barrel having first and second ends, an inner barrel slidable longitudinally within said outer barrel and adapted to support a needle at one end thereof and which needle projects through an aperture in said first end of said outer barrel, said needle being in fluid communication with a fluid retaining chamber of said inner barrel, and a plunger within said chamber and actuable to draw fluid into said chamber and expel fluid from said chamber via said needle, said plunger being connected to an actuating rod extending out from the other end of said inner barrel and the second end of said outer barrel, said outer barrel having first and second spaced retaining means on the inner wall surface thereof, and said inner barrel having latching means for engaging said first or second retaining means and latching said inner barrel in either of two positions relative to said outer barrel, a first said position wherein said needle projects from said outer barrel and is in a useable position, and a second position wherein said needle is fully retracted within said outer barrel, biasing means for biasing said inner barrel towards said second position and said plunger actuating rod having means for contacting said latching means when said plunger is fully depressed to disengage said latching means from said first retaining means whereby said needle moves to said second position wherein said latching means engages said second retaining means and is unable to be re-engaged in said first retaining means.

BRIEF DESCRIPTIONS THE DRAWINGS

In order that the invention may be more readily understood one particular embodiment will now be described with reference to the accompanying drawings wherein:

FIG. 1(a) is an enlargement of the portion of FIG. 1 shown in the circle "A";

FIG. 2 is similar to FIG. 1 but shows the syringe in a first stage of operation;

FIG. 2(a) is an enlargement of the portion of FIG. 2 shown in the circle "B";

FIG. 3 is similar to FIGS. 1 and 2 but shows the syringe in a second stage of operation;

FIG. 4 is similar to FIGS. 1–3 but shows the syringe in a third stage of operation;

FIG. 4(a) is an enlargement of the portion of FIG. 4 shown in the circle "C";

FIG. 5 is similar to FIGS. 1–4 but shows the syringe in a fourth stage of operation;

FIG. 5(a) is an enlargement of the portion of FIG. 5 shown in the circle "D";

FIG. 6 is an exploded perspective view of the syringe of FIGS. 1–5;

FIG. 7 is a view similar to FIG. 1 showing an alternative embodiment of the invention in an initial position;

FIG. 7(a) is an enlargement of the portion of FIG. 7 shown in the circle "E";

FIG. 8 is a view similar to FIG. 7 but showing the syringe in a first stage of operation;

FIG. 8(a) is an enlargement of the portion of FIG. 8 shown in the circle "F";

FIG. 9 is a view similar to FIGS. 7 and 8 showing the syringe in a fourth stage of operation;

FIG. 9(a) is an enlargement of the portion of FIG. 9 shown in the circle "G";

FIG. 10 is a view similar to FIGS. 7–9 showing the syringe in a fifth stage of operation;

FIG. 10(a) is an enlargement of the portion of FIG. 10 shown in the circle "H";

FIG. 11 is an exploded perspective view of the syringe of FIGS. 7–10 inclusive;

DETAILED DESCRIPTION OF THE INVENTION

Figure 1:
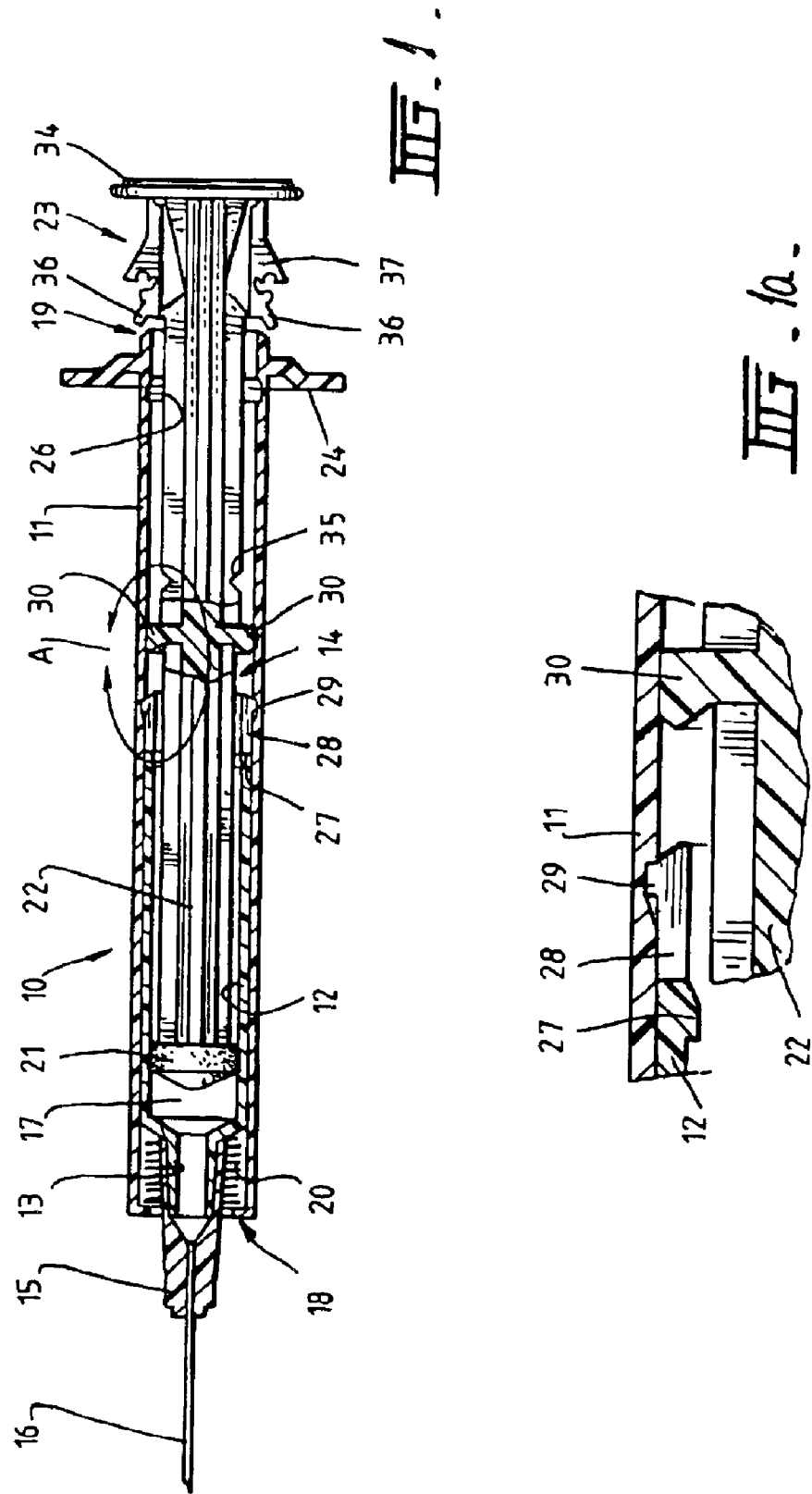
FIG. 1 is a sectional side elevation of a syringe according to one embodiment of the invention, shown in an initial position.
Figure 12:
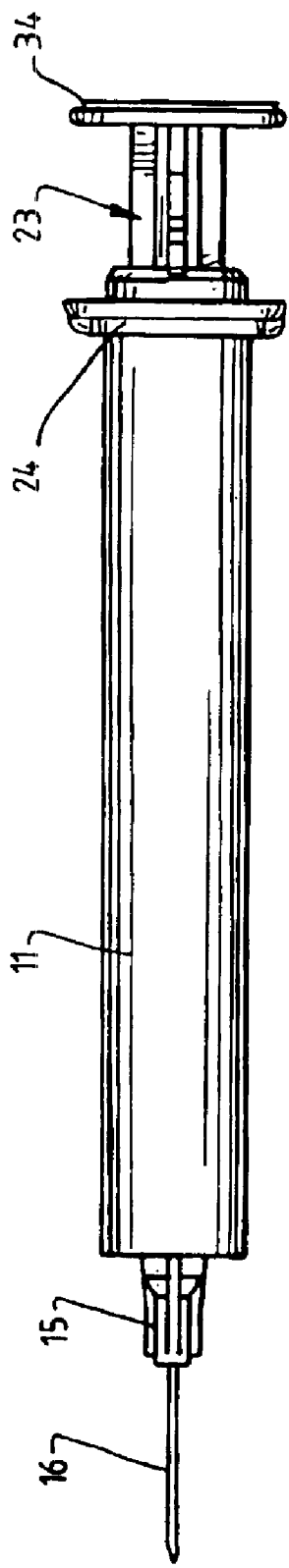
FIG. 12 is a side elevation of a syringe as shown in either of the specific embodiments.
Figure 13:
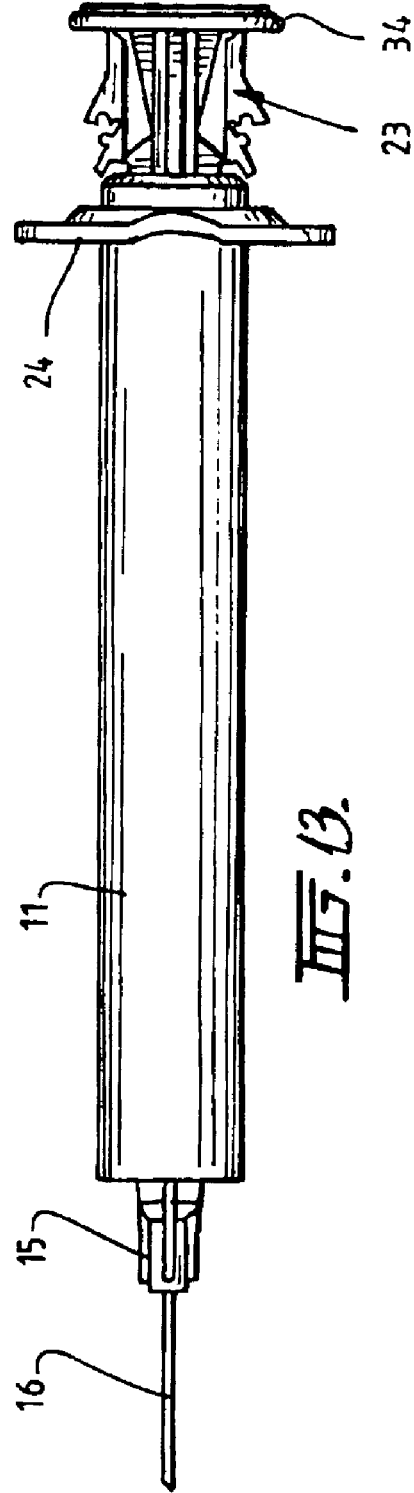
FIG. 13 is similar to FIG. 12 but shows the syringe rotated through 90° about its longitudinal axis.

Throughout the drawings like or similar parts have the same reference number.

The syringe 10 comprises an outer barrel 11 which apart from openings at each end is a completely aperture free cylindrical barrel. An inner barrel 12 fits within the outer barrel 11 in a manner so as to slide longitudinally back and forth within the outer barrel 11 in engagement therewith. The inner barrel 12 has a narrow neck 13 at one end and is open at the opposite end 14. The neck 13 is adapted to accommodate a needle housing 15 incorporating a needle 16. Clearly, the needle 16 is in fluid communication with a chamber 17 within the inner barrel 12. Once fitted to the neck 13 the needle housing 15 and needle 16 project from a first end 18 of the outer barrel 11.

A spring 20 is located inside the first end 18 of the outer barrel 11 and acts on the inner barrel 12 to bias the inner barrel 12 towards a second end 19 of the outer barrel 11.

A plunger 21 is located within the inner barrel 12 and is mounted at one end of a plunger actuating rod 22. The plunger actuating rod 22 enters the second end 19 of the outer barrel and the open end 14 of the inner barrel. The outer end of the plunger rod 22 is provided with a limit catch 23 which will be described later. A flange 24 at the second end 19 of the outer barrel facilitates operation of the syringe. An end flange 34 facilitates operation of the plunger actuating rod 22.

The outer barrel has first and second annular grooves 25 and 26, respectively, in the inner surface thereof. The purpose of the grooves 25 and 26 will become apparent hereinbelow.

The above description describes the main components of a syringe according to the embodiment of FIGS. 1–6 as well as the embodiment of FIGS. 7–11. In the first embodiment the inner barrel 12 has a pair of diametrically opposed longitudinal slits 27 (see FIG. 6) at the open end 14 and the slits 27 define a pair of opposed flexible arms 28. The flexible arms 28 have a lip 29 extending around the extremity thereof for engaging in one or other of the annular grooves 25 and 26. The slits 27 allow the flexible arms 28 to move slightly towards each other for the purpose of disengaging the lip 29 from one or other of the grooves 25 and 26. The configuration of the inner barrel and particularly the flexible arms 28 is more evident in FIG. 6. The plunger actuating rod 22 is provided with an annular skirt 30 having a tapered edge for engaging the respective arms 28 to remove the lips 29 from the respective grooves 25 and 26 as will become apparent hereinbelow.

In the embodiment of FIGS. 7–11, the flexible arms 28 are much narrower in construction (see FIG. 11) and comprise essentially a pair of opposed fingers which extend from the open end 14 of the inner barrel 12. The flexible arms or fingers 28 again have lips 29 which engage in one or the other of the annular grooves 25, 26. In addition, the arms 28 have latch members 31 which extend towards the second end 19 of the outer barrel 11. The actuating rod 22 is provided with an annular skirt 32 similar to the skirt 30 of the previous embodiment but having an inwardly directed ridge 33 extending around the extremity of the skirt. Otherwise, the construction of the syringe in the embodiment of FIGS. 7–11 is the same as in the earlier embodiment.

As mentioned above, the outer end of the plunger actuating rod 22 incorporates a limit catch 23. Essentially, the limit catch prevents the plunger actuating rod 22 and hence the plunger 21 from moving to the forward or needle end extremity of the inner barrel 12 on the first operation of the syringe. Once the plunger actuating rod 22 is forced inwardly towards the needle end of the syringe on the initial occasion the limit catch changes its construction whereby on the next depression of the plunger actuating rod, the plunger is able to move to the forward most extremity of its movement in the inner barrel.

More specifically, on initial depression of the plunger rod 22 fingers 36 of the limit catch 23 engage with the end 19 of the outer barrel 11 and are pivoted from the position shown in FIG. 1 to the position shown in FIG. 2 whereby further movement (depression) of the plunger is prevented. This pivoting is facilitated by a flexible joint between the ends of each finger. The fingers 36 are then locked in this pivoted position. This pivotal movement of the fingers 36 severs a thin membrane 38 (see FIG. 2(a)) which initially holds arms 37 of the limit catch 23 inwardly on the body of rod 22. Consequently, on withdrawal of the plunger rod 22 the arms 37 spring outwardly or spread to the position shown in FIG. 3 wherein tongue and groove 39 locks the arms 37 in the new position. On the next depression of the rod 22 the fingers fail to engage the end of the outer barrel 11 and hence extended depression of the plunger (to the end of inner barrel 12) is facilitated.

Operation of the syringe is as follows. The syringe is packaged after manufacture in a sealed package without the needle housing 15 and needle 16 and is in a condition where the inner barrel and plunger are in a position substantially as shown in FIGS. 1 and 7, respectively. The user removes the syringe from the package and installs a needle housing 15 with attached needle 16 onto the neck 13 of the inner barrel 12. The plunger actuating rod 22 is then depressed by applying thumb pressure on end flange 34 whilst holding the outer barrel 11 between first and second fingers until the actuating rod 22 is fully depressed into the inner barrel 12 and the limit catch 23 prevents further movement. In this position the plunger 21 is almost to the neck 13 of the inner barrel and only a very small chamber exists in the inner barrel between the plunger 21 and the neck 13. It should be noted that at this point movement of the inner barrel 12 relative to the outer barrel 11 is prevented by means of the lip 29 engaging in the annular groove 25 of the outer barrel (see FIGS. 1(a) and 7(a), respectively). Once this initial actuation has taken place, the syringe is in the condition shown in FIGS. 2 and 8 respectively. The purpose of the limit catch is to prevent the lip 29 from being released from the groove 25 on the initial depression of the plunger actuating rod as this would prevent use of the syringe, as will become evident hereinbelow.

The next action is to draw a drug into the inner barrel 12 via the needle 16. The needle 16 is placed in the drug and the plunger is drawn outwardly to a position shown in FIG. 3. The inner barrel still remains firmly fixed relative to the outer barrel.

The next action is to depress the plunger to expel the drug and on this actuation of the plunger actuating rod 22 the plunger moves all the way to the end of the inner barrel 12 as shown in FIG. 4. In other words the limit catch 23 does not restrict the inner movement of the actuating rod 22 on this second depression. In regard to the first embodiment, when the plunger 21 has reached its inner most extremity the protrusions 30 on the rod 22 engage the flexible arms 28 and cam the lip 29 on each arm 28 out from the annular groove 25 as is evident in FIG. 4(a). At this point, as soon as pressure is released from the plunger rod 22, the spring 20 forces the inner barrel towards the second end 19 of the outer barrel, since there is nothing to stop relative movement between the two barrels. Of course this movement relies on the user releasing pressure on the plunger actuating rod 22.

The movement of the inner barrel relative to the outer barrel continues until the inner barrel assumes a position as shown in FIG. 5 wherein the lip 29 of each flexible arm 28 locates in the second annular groove 26. In this position the needle 16 is fully retracted within the outer barrel 11.

As will be evident in FIG. 5 it is possible to depress the plunger actuating rod 22 and cause the inner barrel to disengage the annular groove 26 whereby the needle can be moved outside the first end 18 of the outer barrel. However, such action does not enable the syringe to be re-used because it is not possible to latch the inner barrel, or more specifically the lips 29, into the annular groove 25. This is because the spring 20 holds the inner barrel against the protrusions 30 or ridge 33 whereby the lips 29 remain in a position cammed away from the groove 25.

A notch 35 in the actuating rod 22 enables the part of the actuating rod projecting from the outer barrel to be broken off as a means of preventing further depression of the plunger but even if this action is not performed it is not possible to re-use the syringe.

Operation of the syringe shown in the embodiment of FIGS. 7–11 is very similar in that depression of the actuating rod 22 for the purpose of expelling a drug in the chamber of inner barrel 12 causes the ridge 33 of annular skirt 32 to engage the latch members 31 to again cam the lips 29 from the first annular groove 25 (see FIG. 8(a)). Again the spring 20 causes the inner barrel to move towards the second end 19 of the outer barrel whereby the lips 29 engage in the second annular groove 26 of the outer barrel 11 as is shown more clearly in FIGS. 10 and 10(a). FIGS. 9 and 9(a) show the position of the inner barrel in transit between the two positions.

As will be evident from FIGS. 10 and 10(a), once the inner barrel is latched in the second annular groove 26 it cannot be removed by depressing the plunger actuating rod 22 since engagement between the annular skirt 32, or more particularly the ridge 33 thereon, and the latch member 31 is such that depression of the rod 22 will not cam the latch member 31 from the groove. Therefore further actuation of the plunger or movement of the inner barrel relative to the outer barrel is prevented and the needle is safely retracted within the outer barrel 11. The notch 35 in the actuating rod 22 enables the part of the actuating rod projecting from the outer barrel to be broken off although such action is hardly necessary.

Figure 14:
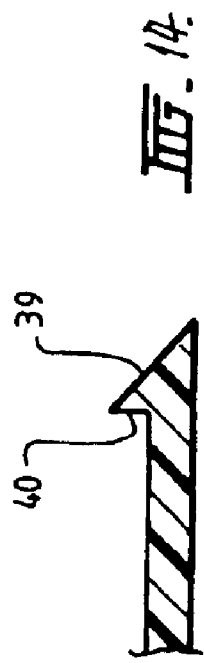
FIG. 14 is an enlarged sectional view of part of a modified flexible arm for use in the described embodiments.

In a modification to the above described embodiments some of the flexible arms 28 on the inner barrel differ to those previously described. A profile of a modified flexible arm 28 is shown in FIG. 14. As well as some of the arms having the modified profile the total number of arms 28 on the inner barrel 12 is increased and preferably comprises a total of at least four such arms comprising at least two of the modified arms. The modified arms 28 are shorter than the other arms which have a profile the same as those shown in FIGS. 1–6 but are thin fingers as in the embodiment of FIGS. 7–11. In the case of a total number of four arms they are uniformly spaced around the barrel 12 with the two long arms being diametrically opposed and the two short arms likewise.

The longer arms are initially latched in the annular groove 25 and are released therefrom in the manner described above, on the first full depression of the plunger. It will be appreciated that the shorter arms 28 are not engaged by the protrusions 30 or skirt 32 as the case may be. Such engagement is with the longer arms. As the plunger retracts the shorter of the arms 28, which are not located in the groove 25 must pass over the groove 25 in moving towards the second end 19. This is achieved by the angled surface 39 being cammed over the edge of the groove 25 nearest the second end 19. In other words, the shorter arms 28 are deformed inwardly towards the longitudinal axis of the syringe as the plunger retracts under the bias of the spring 20 and they glide over the groove 25.

At the second end 19 the longer arms 28 are held away from the groove 26 since they are engaged with the plunger protrusions 30 or skirt 32 under bias from spring 20. The shorter fingers are under no such influence and are able to spring outwardly and engage the groove 26 when the inner barrel reaches its furthermost position towards the second end. Once engaged in the groove 26 the right angled lip 40 of the shorter arms is firmly located in the groove 26 and the inner barrel is thus prevented from ever moving within the outer barrel towards the first end 18. The needle is thus permanently retracted within the outer barrel and the syringe cannot be re-used.

It should be evident that by a combination of the novel latching arrangement between the inner barrel and the outer barrel and the limit catch 23, there is provided a safety syringe which is extremely reliable, relatively inexpensive to manufacture and does not require any positive action to be taken on the part of the user in order to ensure that the syringe is disabled from further use.

Clearly of course many variations may be made to the embodiments described above without departing from the spirit and scope of the invention. Persons skilled in the art will readily envisage alternative mechanisms for latching and de-latching the inner barrel from movement relative to the outer barrel. Various arrangements of the plunger will also be envisaged for the purpose of disengaging the latching mechanism.

What is claimed is:

1. A syringe including:

an outer barrel having first and second ends, an inner barrel slidable longitudinally within said outer barrel and adapted to support a needle at one end thereof which needle projects through an aperture in said first end of said outer barrel, said needle being in fluid communication with a fluid retaining chamber of said inner barrel, and a plunger within said chamber and actuable to draw fluid into said chamber and expel fluid from said chamber via said needle, said plunger being connected to an actuating rod extending out from the other end of said inner barrel and the second end of said outer barrel, said outer barrel having retaining means on an inner wall surface thereof, and said inner barrel having latching means for engaging said retaining means and latching said inner barrel in either of two positions relative to said outer barrel, a first said position being one in which said needle projects from said outer barrel and is in a useable position, and a second said position being one in which said needle is fully retracted within said outer barrel, biasing means for biasing said inner barrel towards said second position and said plunger actuating rod having means for contacting said latching means when said plunger is fully depressed to disengage said latching means from said retaining means whereby said needle moves to said second position wherein said latching means engages said retaining means and is permanently retained, and wherein a limit catch is provided on said actuating rod, said limit catch preventing said plunger from being fully depressed and disengaging said latching means from said retaining means on an initial actuation of said plunger but allowing said plunger to be depressed sufficiently to disengage said latching means on the next plunger depression.

2. A syringe as defined in claim 1 characterised in that said retaining means comprises first and second spaced grooves.

3. A syringe as defined in claim 1 characterised in that said needle is mounted in a needle supporting neck connected to said one end of said inner barrel.

4. A syringe as defined in claim 2 characterised in that said grooves are annular grooves in the inner wall surface.

5. A syringe as defined in claim 2, characterised in that, when said inner barrel moves to said second position said latching means is permanently engaged in said second groove.

6. A syringe as defined in claim 2, characterised in that, said means for contacting said latching means when said plunger is fully depressed comprises an annular skirt depending from the plunger actuating rod, a rim of said skirt being adapted to contact said latching means and disengage same from said first groove.

7. A syringe as defined in claim 6, characterised in that, said latching means comprises a plurality of flexible arms extending longitudinally from the other end of said inner barrel in a direction towards said second end of said outer barrel, said arms comprising one or more long arms and one or more short arms, said long arm or arms having a protrusion for engaging said first groove to prevent movement of said inner barrel to said second position, said short arm or arms having a protrusion configured for moving over said first groove without engaging therein and engaging in said second groove to become permanently retained therein, and said long arm or arms having means for contacting said annular skirt when said plunger is fully depressed to remove said protrusions of said long arm or arms from said first groove whereby said inner barrel is forced, by said biasing means, to said second position.

8. A syringe as defined in claim 7, characterised in that there are two diametrically opposed said long arms and two diametrically opposed said short arms equally spaced around said inner barrel.

9. A syringe as defined in claim 8, characterised in that, said annular skirt has an inwardly directed annular ridge at the edge thereof for engaging said long arms to remove said protrusions from said first groove when said plunger is fully depressed.

10. A syringe as defined in claim 1, characterised in that, said biasing means is a compression spring located between said outer and inner barrels and bearing on the first end of said outer barrel and a flange on the outer surface of said inner barrel.

11. A syringe as defined in claim 1 characterised in that, said limit catch comprises respective articulated fingers mounted on opposite sides of said plunger actuating rod at an outer end thereof, each finger initially extending in a straight configuration parallel with a longitudinal axis of said rod and being connected to said rod at each end of the finger, the configuration of the fingers being such that initial actuation of said rod causes the end of each finger directed towards said outer barrel to bear on the second end of said outer barrel causing fracturing of the connection between an inner end of the finger and the rod, and bending of the finger to a generally right angled configuration preventing further inward movement of the plunger, said fingers being locked in said right angled configuration and, upon withdrawal of said rod said fingers pivoting away from said rod by means of a bias in the connection between the fingers and the outer end of the rod whereby on the following actuation of said plunger actuating rod said fingers do not engage the second end of the outer barrel in a manner preventing full depression of said rod.

* * * * *